(12) United States Patent
Krabbe

(10) Patent No.: US 11,631,476 B2
(45) Date of Patent: Apr. 18, 2023

(54) COMPUTER PROGRAM PRODUCT, DEVICE, SYSTEM AND METHOD FOR GATHERING RESPONDENT INPUT

(71) Applicants: Rijksuniversiteit Groningen, Groningen (NL); Academisch Ziekenhuis Groningen, Groningen (NL)

(72) Inventor: Paul F. M. Krabbe, Zeist (NL)

(73) Assignees: Rijksuniversiteit Groningen, Groningen (NL); Academisch Ziekenhuis Groningen, Groningen (NL)

( * ) Notice: Subject to any disclaimer, the term of this patent is extended or adjusted under 35 U.S.C. 154(b) by 175 days.

(21) Appl. No.: 16/343,561

(22) PCT Filed: Oct. 19, 2017

(86) PCT No.: PCT/NL2017/050683
§ 371 (c)(1),
(2) Date: Apr. 19, 2019

(87) PCT Pub. No.: WO2018/074924
PCT Pub. Date: Apr. 26, 2018

(65) Prior Publication Data
US 2020/0051672 A1 Feb. 13, 2020

(30) Foreign Application Priority Data
Oct. 20, 2016 (EP) .................................... 16194795

(51) Int. Cl.
*G16H 10/20* (2018.01)
*G16H 10/60* (2018.01)
(Continued)

(52) U.S. Cl.
CPC ......... *G16H 10/20* (2018.01); *G06F 3/04842* (2013.01); *G06F 16/24578* (2019.01);
(Continued)

(58) Field of Classification Search
CPC ........ G16H 10/20; G16H 10/60; G16H 50/20; G16H 50/30; G06F 16/24578; G06F 3/04842
See application file for complete search history.

(56) References Cited

U.S. PATENT DOCUMENTS 8,340,982 B2    12/2012  Bjorner et al.
2002/0035486 A1*  3/2002  Huyn ....................... G09B 7/02
                                                            705/3
(Continued)

OTHER PUBLICATIONS

Paul F. M. Krabbe, A Generalized Measurement Model to Quantify Health: The Multi-Attribute Preference Response Model, 8(11) PLOS ONE 1-12 (Nov. 21, 2013) (Year: 2013).*
(Continued)

*Primary Examiner* — Evangeline Barr
*Assistant Examiner* — Jordan L Jackson
(74) *Attorney, Agent, or Firm* — Banner & Witcoff, Ltd.

(57) ABSTRACT

A computer program product for gathering respondent input for determining a ranking of states each characterized by a set of selected levels each associated to an attribute. The interface mechanism provides for inputting selected attribute levels of a respondent state and for ranking of comparable alternative states determined in response to the inputted respondent state, in comparison with that respondent state. The alternative states are each displayed as the set of attributes with the associated set of alternative levels simultaneously and with an input field for inputting a preference indication of the shown alternative state compared with the respondent state. This allows the respondent input to be entered with very few input actions and little switching (Continued)

between screens. Only the selected attribute levels of the respondent state and the rankings and identifications of the determined alternative states need to be transmitted to the central computer.

14 Claims, 2 Drawing Sheets

(51) Int. Cl.
  *G16H 50/30* (2018.01)
  *G16H 50/20* (2018.01)
  *G06F 16/2457* (2019.01)
  *G06F 3/04842* (2022.01)

(52) U.S. Cl.
  CPC ............ *G16H 10/60* (2018.01); *G16H 50/20* (2018.01); *G16H 50/30* (2018.01)

(56) References Cited

U.S. PATENT DOCUMENTS

| | | |
|---|---|---|
| 2010/0235226 A1 | 9/2010 | Keil et al. |
| 2013/0144645 A1 | 6/2013 | Bjorner et al. |
| 2014/0081898 A1 | 3/2014 | Saigal et al. |
| 2014/0095513 A1* | 4/2014 | Kriebel ............. G06Q 30/0203 707/748 |
| 2019/0019573 A1* | 1/2019 | Lake .................... A61B 5/4842 |

OTHER PUBLICATIONS

Aul F. M. Krabbe, A Generalized Measurement Model to Quantify Health: The Multi-Attribute Preference Response Model, 8(11) PLOS ONE 1-12 (Nov. 21, 2013) (Year: 2013).*

Krabbe PFM, A generalized measurement model to quantify health: the multi-attribute preference response model, Pios One, 2013; vol. 8, Isssue 11, e7949.

Krabbe PFM, A generalized measurement model to quantify health: the multi-attribute preference response model, In: A.B. Badiru, L.A. Racz (eds.), Handbook of Measurements: Benchmarks for Systems Accuracy and Precision. CRC Press, Boca Raton, Nov. 2015 Title Page, Bibliographic page, pp. 239-260.

Krabbe PFM, The Measurement of Health and Health Status: Concepts, Methods and Applications From a Multidisciplinary Perspective, San Diego: Elsevier/ Academic Press, 2016 Title page, Bibliographic page, pp. vii-xiv and 322-324.

* cited by examiner

COMPUTER PROGRAM PRODUCT, DEVICE, SYSTEM AND METHOD FOR GATHERING RESPONDENT INPUT

FIELD AND BACKGROUND OF THE INVENTION

The invention relates to a computer program product, a device, a system and a method for gathering respondent input for determining a ranking of a plurality of states each characterized by a set of selected levels each associated to an attribute of a set of attributes associated to said state.

In the field of the gathering of respondent input for determining the perceived quality of states that are characterized by levels of a plurality of distinct attributes, it is a challenge to gather respondent assessments of the perceived quality of these states that are realistic and unbiased in a quick and efficient manner. In particular if the states are characterized by attributes that are a feature of a personal situation, such as health-related quality of life assessments (HRQoL), social well-being, economic well-being, personal development, housing, travel or family or work situation.

U.S. Pat. No. 8,340,982 discloses assessing the impact of various ailments on the HRQoL by registering responses regarding effects of a current ailment on HRQoL. These types of assessments based on Likert-type items that measure the frequency or intensity of complaints in any given health domain. However, this provides little information on the perceived severity of these ailments.

In Krabbe PFM, A generalized measurement model to quantify health: the multi-attribute preference response model, *Plos One*, 2013; Vol. 8, Issue 11, e79494 and in Krabbe PFM. A generalized measurement model to quantify health: the multi-attribute preference response model. In: A. B. Badiru, L. A. Racz (eds.), Handbook of Measurements: Benchmarks for Systems Accuracy and Precision. CRC Press, Boca Raton, November 2015, two measurement tools, the discrete choice and the Rasch model (a basic model in Item Response Theory), are combined in an integrated measurement model, called the multi-attribute preference response (MAPR) model. This model transforms subjective individual rank data into a metric scale using responses from respondents in various situations, e.g. patients in various certain health states. Its measurement mechanism largely prevents biases such as adaptation and coping effects. The MAPR model can be applied to a wide range of research problems. The term 'preference' generally denotes the (relative) 'desirability' of something or someone. Within a preference-based measurement framework, distinct attributes used to characterize the state of each respondent are assigned weights. These are produced by specific measurement strategies that elucidate the relative importance of attributes. Unlike the conventional instruments that have been developed under classical test theory and item response theory, preference-based measurement does not concern the frequency or intensity of complaints, or abilities in any given domain as such. Further details regarding the MAPR model and other measurement strategies used in health outcome measurement can be found in Krabbe PFM, *The Measurement of Health and Health Status: Concepts, Methods and Applications from a Multidisciplinary Perspective*, San Diego: Elsevier/Academic Press, 2016.

SUMMARY OF THE INVENTION

It is an object of the present invention to provide a solution that allows gathering responses and in particular rank data from a large number of respondents quickly and efficiently, and requires very few input actions from each respondent and only a small amount of data communication.

According to the invention, this object is achieved by providing a computer program product for gathering respondent input for determining a ranking of a plurality of states each characterized by a set of selected levels each associated to an attribute of a set of attributes associated to the state, the computer program product being in microprocessor readable form and arranged for, when stored in a memory of a device, further including a display, a communication port and a microprocessor for controlling the display and arranged for communicating, via the communication port, with a central computer and when executed by the microprocessor:

causing the display to show the attributes of the set and allowing selecting respondent levels for the attributes;

storing the set of selected respondent levels for the attributes as a respondent state;

determining a plurality of alternative ones of the states in accordance with the respondent state or outputting the respondent state to the central computer and receiving back a plurality of alternative ones of the states determined in accordance with the respondent state by the central computer;

causing the display to show each of the determined alternative states as the set of attributes with the associated set of alternative levels simultaneously and with at least one input field for inputting a preference indication of the shown alternative state compared with the respondent state on the display; and outputting the respondent state and inputted respondent preference indications compared with the respondent state for each of the determined alternative states to the central computer.

The invention can also be embodied in:

a device including a display, a communication port, a memory and a microprocessor for controlling the display and arranged for communicating, via the communication port, with a central computer and a computer program product as described above stored in the memory, in a system including a central computer, a device including a display, a communication port, a memory and a microprocessor for controlling the display and arranged for communicating, via the communication port, with the central computer and a computer program product as described above, stored in the memory of the device, in a memory of the central computer or partially in the memory of the device and partially in the memory of the central computer, and in a method for gathering respondent input for determining a ranking of a plurality of states each characterized by a set of selected levels each associated to an attribute of a set of attributes associated to the state, using a plurality of devices each including a display, a memory, a computer program stored in the memory, a communication port and a microprocessor for controlling the display and each arranged for communicating, via the communication port, with a central computer, the microprocessors each:

causing the display to show the attributes of the set and allowing selecting respondent levels for the attributes;

storing the set of respondent levels of the attributes as a respondent state;

determining a plurality of alternative ones of the states in accordance with the respondent state or outputting the respondent state to the central computer and receiving back a plurality of alternative ones of the states determined in accordance with the respondent state by the central computer;

causing the display to show each of the determined alternative states as the set of attributes with the associated set of alternative levels simultaneously and with at least one input field for inputting a preference indication of the shown alternative state compared with the respondent state on the display; and outputting the respondent state and inputted respondent preference indications compared with the respondent state for each of the determined alternative states to the central computer.

The interface mechanism provides for inputting selected attribute levels of a respondent state and for ranking of comparable alternative states determined in response to the inputted respondent state, in comparison with that respondent state on a device communicating with a central computer. The determined alternative states are each displayed on the display, preferably one at a time, as the complete set of attributes together with the associated set of alternative levels of that alternative state (i.e. of each determined alternative state, all attributes and all associated levels of these attributes are simultaneously displayed) and with at least one input field for inputting a preference indication (e.g., better or worse, more or less, in favor or not in favor) of the shown alternative state compared with the respondent state. This allows respondent input to be entered with very few input actions and little switching between screens. Only the selected attribute levels of the respondent state and the rankings and identifications of the determined alternative states need to be transmitted to the central computer.

The determination of alternative states to be assessed by individual respondents is preferably a selection of possible alternative states within a given amount of changes relative to the respondent state, to avoid answers of decreasing relevance due to declining concentration and interest by the respondent. For obtaining a meaningful sample, the distribution of determined alternative states amongst possible alternative states (and preferably also the order of presentation of alternative states) for respondents with the same respondent state should be randomized. If the plurality of alternative ones of the states to be presented to the respondent for assessment is determined by each of the devices only, all of the respondent input can be gathered without any communication between the device and the central computer. This allows the respondent input to be gathered on the device while the device is off-line. The respondent state, the plurality of alternative states, and the inputted preferences regarding these alternative states can be uploaded to the central computer when a connection is available, or when a low-cost connection, such as a Wifi connection is available. It can thus be warranted to potential respondents that participating does not incur any significant costs and the risk that a respondent does not answer all the questions, because alternative states are not presented due to problems with connecting to the central computer are avoided. Furthermore, communication is simplified and made more reliable, because all respondent data can be transmitted as a single data string.

When gathering the respondent input from a plurality of devices, selection of alternatives states based on identical respondent state of different respondents should preferably be varied, but distributed randomly but evenly over respondents. If the determination of alternatives states based on identical respondent state of different respondents is furthermore carried out by randomized selection by the microprocessor, the entire collection of respondent data including the in-part randomized determination of alternative states that are both tied to the respondent state and randomly selected can be carried out while the respondent's device is off-line.

Particular elaborations and embodiments of the invention are set forth in the dependent claims.

Further features, effects and details of the invention appear from the detailed description and the drawings.

BRIEF DESCRIPTION OF THE DRAWINGS

FIG. 2 is an image of a user interface for inputting selected levels of a respondent state;

FIG. 3 is the image of FIG. 2 during toggling to another selected level; and

FIG. 4 shows an image a further user interface representing an alternative state.

DETAILED DESCRIPTION

Figure 1:
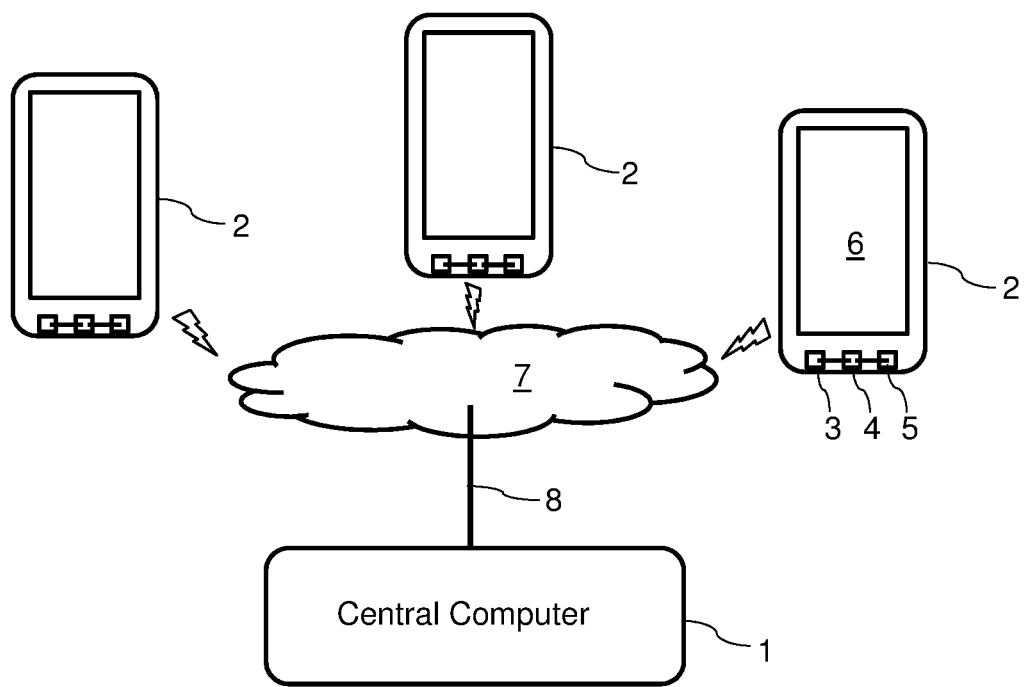
FIG. 1 is a schematic representation of a system according to the invention.

FIG. 1 shows an example of a system according to the invention including a plurality of distributed devices 2 and a central computer 1 arranged for communication with the devices 2 via a network 7 which may for instance include a cellular telecommunications network and the Internet. The central computer 1 is connected to the network 7 via a connection 8. In the present example, the distributed devices 2 are cellular phones with a touch screen also referred to as smart phones. However, the distributed devices may also include other computer devices for personal use, such as tablets or personal computers.

The devices 2 each include a touch screen display 6, a communication port 3, a memory 5 and a microprocessor 4 for controlling the display 6 and arranged for communicating, via the communication port 3, with the central computer 1. A computer program product according to the invention is stored in the memory 5 so that it is in a non-transitory form. The computer program may also be completely or partially stored in the central computer and for instance be accessible using a web browser program running on the distributed device. It is noted that the graphic user interface may additionally or alternatively be operable by controlling the position of a displayed cursor, for instance using a mouse, touchpad or cursor displacement control keys.

The computer program product is for gathering respondent input for determining a ranking of states each characterized by a set of selected levels each associated to an attribute of a set of attributes associated to the state. The states may for instance be states in a MAPR model as described in Krabbe PFM, A generalized measurement model to quantify health: the multi-attribute preference response model, *Plos One,* 2013; Vol. 8, Issue 11, e79494. The MAPR model is a generic statistical model that, based on the input from many respondents estimating their relative positions in relationship to states in which other respondents are or may be. Preference responses (whether respondents consider their own situation/condition better or worse than alternative situations/conditions) are collected in interaction with a user interface controlled by the computer program product being executed and sent to the central server. On the central server, a computer program processes the received data in accordance with the MAPR model structure. Preference values (variously called utilities, strengths of preferences, indices, or weights) that these methods generate are preferably assumed to be unidimensional on a linear scale, so that differences between values of assessment of respondent states can be assumed to correspond to increments of difference in quality of these states, which implies that the values should be interval-level or cardinal data. Thus, the differences between values indicate true differences (e.g., if a patient's value increases from 40 to 60, this increase is the same as an increase from 70 to 90). Preference-based measurement can be very convenient because it produces one overall numerical score, which makes analyzing and interpreting results a straightforward procedure. The computer program product is in microprocessor readable form and, when executed by the microprocessor 4, basically causes the following steps to be carried out.

Figures 2, 3, 4:
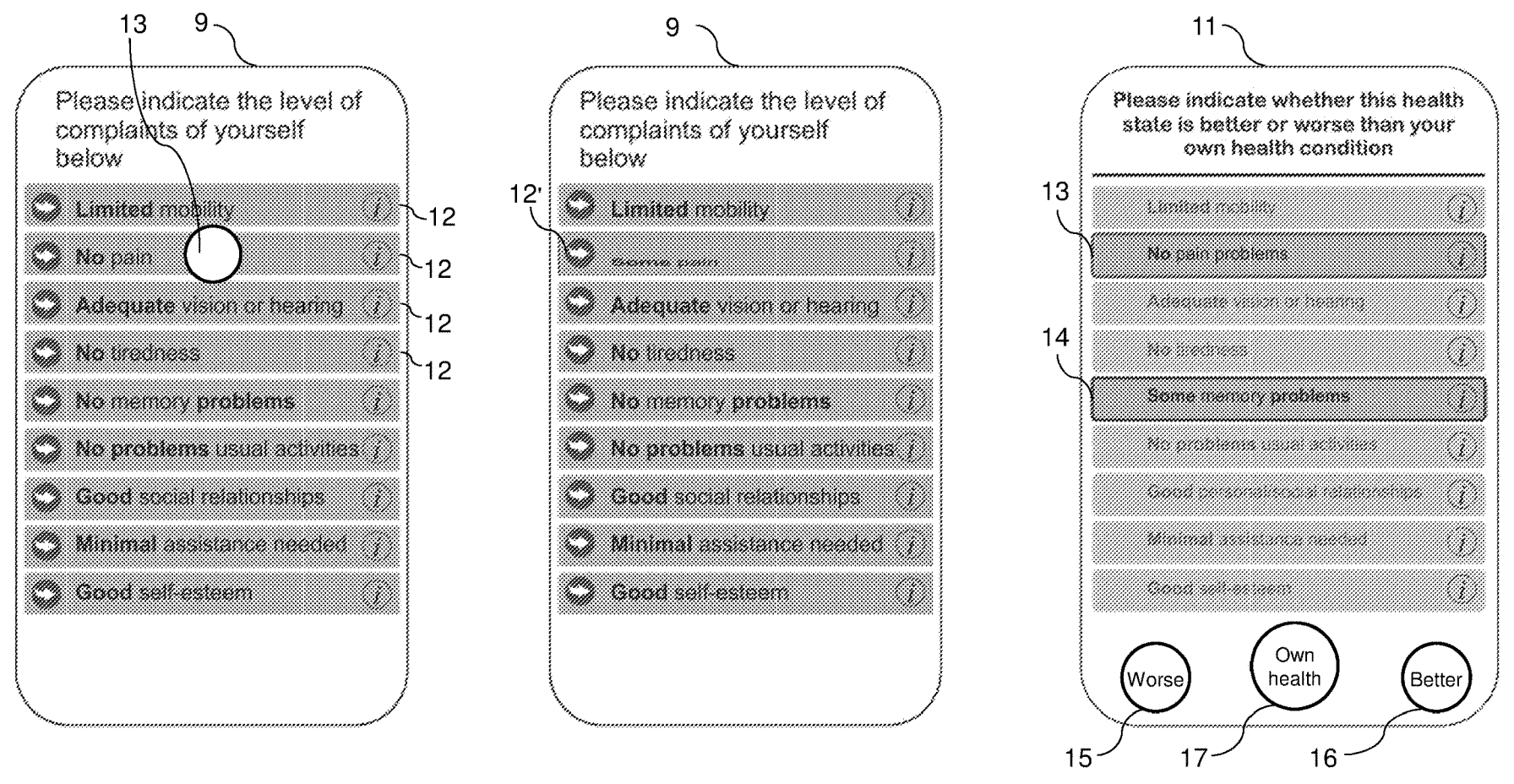

As illustrated by the example of user interface 9 in FIG. 2, the display 6 is controlled to show attributes 12 of the set of attributes and allowing respondents to select levels for the attributes, which they feel best match their personal scores on those respective attributes. This is illustrated by touching the display in an area 13 of the user interface that causes the attribute line 12 covered by that touched area 13 to toggle from a level "no pain" to a level "some pain". It is noted that levels may be descriptions that are ranked on a scale as in the present example, but may also be numeric values or grades. If the attribute pain is touched again, it is toggled to the next level, which may be repeated to scroll through, for instance until it again shows "no pain".

After levels for all the attributes of the set have been selected, the set of respondent selected levels of the attributes is stored in the memory 5 as a respondent state. Alternatively or additionally, the computer program may also control the microprocessor 4 so that the respondent state is outputted to the central computer, preferably in association with a previously inputted user identification. The next step may then be initiated by for instance a swiping movement over the display 6 or operating a next input field of the user interface (not shown).

In accordance with the stored respondent state, a plurality of alternative states is determined. The alternative states are determined by the microprocessor under control of the computer program to each differ from the selected respondent state with respect to a limited number of attributes (e.g., two, three or four) only and preferably also by only one level for attributes to which a different level is assigned, so that the respondent can easily imagine the impact the change would have, starting off from the respondent state with which the respondent is familiar, since it is the respondent's current (self-assessed) state. The alternative states may for instance be determined by defining the alternative states starting off from the respondent states or be selected from alternative states stored in the memory 5.

A routine for determining alternative states may for instance start from a respondent's inputted personal state (condition or perception) and generate alternative states differing from the inputted state by a randomly selected limited subset of the attributes, the levels of these attributes preferably being set to balance worse levels on one or more attributes against better levels on one or more other ones of the attributes of the subset of attributes with differing levels.

This routine may be part of the computer program executed by a device of the user, so an entire session response can be carried out without communication with the central computer (i.e. also in absence of data communication facilities). The respondent state and the subsets of attributes with the differing levels of each alternative state can be transmitted to the central computer in association with the selected score (better or worse than the personal state) for that alternative state and the respondent levels defining the self-classification of the personal state of the respondent.

In most cases, the number of possible alternative states that differ from the respondent state by a difference within a predetermined range (e.g. one attribute better and one attribute worse) will be too large to be considered by the respondent to which the respondent state applies. Therefore, for each respondent, the number of alternative states to be presented to that respondent will have to be smaller than the number of the possible alternative states, so a selection of alternative states will have to be made for each respondent. To nevertheless have all possible alternative states of each respondent state assessed by one or more respondents, such a selection is preferably varied over the possible alternative states, such that different alternative states will be presented to different respondents to which the same respondent state applies.

Preferably, the plurality of alternative ones of said states is determined by each of the devices only, so that no communication with the central computer is necessary between entry of data determining the respondent state and successive presentation of the alternative states.

To achieve an even and representative distribution of presented alternative states associated to a given respondent state over all possible alternative states that can be derived from that alternative states, the determination of alternative states to be presented is preferably carried out by the microprocessor by randomized selection. Thus, communication with the central computer is also not necessary for the in-part randomized determination of alternative states to be presented to a respondent.

The randomized selection may for instance be achieved by randomly selecting attributes for which a changed value is chosen in the alternative state. Such a selection preferably also takes into account that attributes for which an extreme best or worst value has been entered in the respondent state can only be changed in one sense (either worse or, respectively better).

It is however also possible to achieve a randomized selection by the microprocessor by first determining all possible alternative states on the basis of the respondent state and subsequently selecting alternative states to be presented therefrom on the basis of a value of a dispersion variable that has previously been assigned by the central computer. Instead of a single dispersion variable, a plurality of dispersion variables may be assigned to each device and for instance be used each for determination of one alternative state to be selected.

Another option, which does require communication between the central computer 1 and the device, is to determine alternative states centrally by the central computer 1 in response to the outputting of the respondent state to the central computer 1 and transmitting data representing the alternative states back to the device.

Communication with the central computer is preferably provided for in the course of initialization (start-up or update the computer program stored in the user device). That may precede use of the computer program (e.g., after entering an identification code) or during use of the computer program. Preferably, the initialization appoints the respondent to a particular investigation and determines what information should is offered to the respondent (e.g., instructions regarding the use of a measuring instrument, descriptions of the attributes and their levels, language), all text, including the buttons preferably being dynamic. For example, a Dutch language interface for a chronic pain (content) study in Groningen or an English language interface for an infant health study (to be filled out by the respective infant's mothers).

Next, as shown in user interface 11 the display 6 is caused to show each of the alternative states as the set of attributes 12 with the associated set of alternative levels simultaneously and with input fields 15, 16 for inputting a preference indication for the shown alternative state compared with the respondent state on the display 6. Instead of separate input fields for inputting opposite judgments (e.g., a "better" field and a "worse" field), a single preference indication input field may be provided, for instance in the form of a ruler scale that could also allow input of judgments selected from more than two values (e.g., by shifting a slider field along a scale or to a "better" or a "worse" field). After a preference choice has been inputted for a shown alternative state, the user interface displays the next alternative state automatically, until all alternative states determined in response to the respondent state have been displayed and rated.

After respondent preferences have been inputted for all alternative states presented to the respondent, the inputted respondent preference indications compared with the respondent state for each of the alternative states are outputted to the central computer 1. At the central computer 1, the respondent preference indications received from a large number of respondents can be processed into a single state preference ranking and/or appreciation score for the population of respondents, for instance using the aforementioned MAPR model.

As is shown in FIG. 4, the display 6 is controlled to show each of the alternative states with a mark-up 13, 14 of attributes of that alternative state of which the level differs from the respondent state. Other attributes of that alternative state of which the level has not been changed relative to the level in the respondent state are displayed with less contrast, darker and/or in less intense colors so that these attributes are displayed less prominently.

The mark-ups 13, 14 indicates, for each level of the shown alternative state differing from the corresponding level of the respondent state, whether the level of the shown alternative state is better or higher or worse or lower than the respondent level selected for the same attribute of the respondent state.

In the present example, not only the full attribute set of the alternative states, but also the full set of attributes for allowing the selection of the respondent levels for the attributes 12 is shown simultaneously on the display. This allows also all the attributes 12 of the respondent state to be seen without switching screens and facilitates becoming familiarized with the overview of the set of attributes, so that more reliable and meaningful responses can be expected.

For the same purpose, the display 6 is controlled to display the attributes 12 of the set for allowing the selection of the respondent levels for the attributes and of the alternative states with the attributes in the same order and also in the same format. The presentation of the attributes may be varied from respondent to respondent in a random manner. For instance, by varying the order (e.g., the top-down order) in which attributes are presented, biases resulting from a tendency to pay more attention to attributes as they are presented higher up in a list can be neutralized, at least to some extent.

Since the attributes 12 of the set for allowing the selection of the respondent levels for the attributes is displayed with selectable levels selectable in toggle or pull-open fields, also a substantial number of attributes can be displayed in one screen, while allowing the selection of levels for each attribute 12 in the same single screen and without affecting overview over the attributes of the current respondent status.

After determination or receipt of the alternative states, alternatingly displaying of the alternative state and the respondent state to further facilitate comparison can be achieved easily, because the user interfaces showing the alternative states each include a toggle field 17 for switching from displaying of the shown alternative state to displaying of the respondent state or vice versa. The toggle field 17 is then also displayed in the user interface showing the respondent state.

For quick assessment of a plurality of alternative states by the respondent a next one of the alternative states is preferably displayed automatically in response to an input via the preference indication fields 15, 16, so that no separate user input is needed for causing the next alternative state to be shown.

The invention claimed is:

1. One or more non-transitory media storing instructions for gathering respondent input for determining a ranking of a respondent state to a plurality of alternate states, wherein each state is characterized by a plurality of attributes, where each attribute comprises a selected level from selectable levels, the instructions, when executed by one or more microprocessors of a device, cause the one or more microprocessors to perform steps comprising:
receiving, from a remote computer, first information comprising a quantity of states;
storing, in a memory of the device, the received first information;
causing a display, of the device, to show the plurality of attributes for a state;
receiving respondent selections of a level for at least one of the displayed attributes;
storing, in the memory of the device, the selected respondent levels as the respondent state;
generating, by the device without contacting the remote computer, a plurality of the alternate states via determining, based on the selected respondent levels of the attributes of the respondent state and for each alternate state, a plurality of alternative levels of the respective attributes;
causing the display to show, for each alternate state, the attributes with the alternate levels of the alternate state and at least one preference indication field, on the display, for receiving a preference indication of the displayed alternate state relative to the respondent state;
receiving, based on user interactions with the at least one preference indication field, respondent preference indications; and
transmitting, to the central computer, the respondent state, the plurality of alternative levels of the respective attributes, and received respondent preference indications.

2. The one or more non-transitory media according to claim 1, wherein the instructions are further configured to, when executed, perform steps comprising:
causing, by the one or more microprocessors of the device, to display the plurality of alternate states,
wherein a quantity of the determined alternate states is fewer than all possible alternative states.

3. The one or more non-transitory media according to claim 2, wherein the instructions for determining the plurality of alternate levels for each alternate state are further configured to, when executed, perform steps comprising:
randomly selecting a level for one or more attributes of each alternate state.

4. The one or more non-transitory media according to claim 1, wherein the instructions causing the display to show the alternate levels of the alternate state are further configured to, when executed, perform steps comprising:

causing the display to show, for each of the alternate states, a mark-up of specific attributes of the displayed alternate state where levels of the specific attributes of the displayed alternate state differ from levels of the respective specific attributes in the respondent state.

5. The one or more non-transitory media according to claim 1, wherein the instructions to cause display to show the plurality of attributes are further configured to, when executed, perform steps comprising:

causing simultaneous display of the attributes for allowing the respondent selection of the levels of the attributes.

6. The one or more non-transitory media according to claim 1, wherein the instructions are further configured to, when executed, perform steps comprising:

causing, after obtaining the plurality of alternate states and via respondent interaction with a displayed toggle field, an alternating display between one of the alternate states and the respondent state.

7. The one or more non-transitory media according to claim 1, wherein the instructions to cause display of the attributes with the alternate levels of the alternate state are further configured to, when executed, perform steps comprising:

causing, in response to an input via the preference indication field, displaying a next one of the alternative states.

8. The one or more non-transitory media according to claim 1, wherein the instructions to cause display of the attributes with the alternate levels of the alternate state are further configured to, when executed, perform steps comprising:

causing display of the preference indication field and an alternative preference indication field.

9. A device comprising
a display,
a communication port,
a memory and
one or more microprocessors for controlling the display and arranged for communicating, via the communication port, with a central computer and controlled based on computer instructions, according to claim 1, stored in the memory.

10. A system comprising
a central computer; and
a device comprising:
  a display,
  a communication port,
  a memory, and
  one or more microprocessors for controlling the display and arranged for communicating, via the communication port, with the central computer,
wherein the device is configured to store the instructions according to claim 1.

11. A method for gathering respondent input for determining a ranking of a respondent state to a plurality of alternate, wherein each state is characterized by a plurality of attributes, where each attribute comprises a selected level from selectable levels, the method comprising:

receiving, from a remote computer, first information comprising a quantity of states;

storing, in a memory of the device, the received first information;

causing a display of a device to show the plurality of attributes for a state;

receiving respondent selections of a level for at least one of the displayed attributes;

storing, in the memory of the device, the selected respondent levels as the respondent state;

generating, by the device without contacting the remote computer, a plurality of alternative states via: determining, based on the selected respondent levels of the attributes of the respondent state and for each alternate state, a plurality of alternative levels of the respective attributes;

causing the display to show, for each alternate state, the attributes with the alternate levels of the alternate state and at least one preference indication field, on the display, for receiving a preference indication of the displayed alternate state relative to the respondent state;

receiving, based on user interactions with the at least one preference indication field, respondent preference indications; and transmitting, to the central computer, the respondent state, the plurality of alternative levels of the respective attributes, and received respondent preference indications.

12. A method according to claim 11,
wherein the plurality of alternative states is determined by the device, and
wherein a quantity of the determined alternative states is fewer than all possible alternative states.

13. A method according to claim 12,
wherein the determination of the plurality of alternative states is performed, on one or more microprocessors of the device, via randomly selecting a level for one or more attributes of each alternate state.

14. One or more non-transitory media storing instructions that, when executed by one or more microprocessors of a device, cause the one or more microprocessors to perform steps comprising:

receiving, from a remote computer, first information comprising a quantity of states, wherein each state comprises a plurality of attributes, wherein each attribute comprises a level from available levels;

storing, in a memory of the device, the received first information;

generating, by the device, a first user interface comprising a plurality of fields, wherein each field corresponds to one attribute of a state;

receiving, for each field, user selection of a level from available levels for each attribute;

storing, in the memory of the device and as a user state, the selected levels for the attributes;

repeatedly performing steps, without contacting the remote computer, comprising:

selecting, from the user state, two of the attributes;

generating, by the one or more processors of the device, an alternative level, for each of the selected two attributes, of the available levels, wherein the alternative level is different from the user selection of the level for that respective attribute, wherein a combination of the selected attributes with their alternative levels and remaining attributes, of the user state, with the user selected levels comprise an alternative state;

modifying, by the one or more processors of the device and based on the alternative state, the first user interface to display the alternative state;

generating, by the one or more processors of the device, a second user interface comprising at least one field configured to receive a user selection of the alternative state relative to stored user state;

receiving the user selection of the comparison; and
storing the user selection of the alternative state;

transmitting, to the remote computer, the stored user state, the alternative levels of the selected two attributes, and the user selection of the alternative state; and receiving, from the remote computer, a comparison of the user state and the user selection of a reconstructed alternative state with user states of other users and user selections of reconstructed alternative states of the other users.

* * * * *